United States Patent
Begg

(10) Patent No.: US 11,547,481 B2
(45) Date of Patent: Jan. 10, 2023

(54) SYSTEMS AND METHODS FOR LAPAROSCOPIC PLANNING AND NAVIGATION

(71) Applicant: Covidien LP, Mansfield, MA (US)

(72) Inventor: Nikolai Begg, Wayland, MA (US)

(73) Assignee: Covidien LP, Mansfield, MA (US)

(*) Notice: Subject to any disclaimer, the term of this patent is extended or adjusted under 35 U.S.C. 154(b) by 613 days.

(21) Appl. No.: 15/867,779

(22) Filed: Jan. 11, 2018

(65) Prior Publication Data

US 2019/0209241 A1 Jul. 11, 2019

(51) Int. Cl.
| | | |
|---|---|---|
| A61B 34/10 | (2016.01) | |
| A61B 17/34 | (2006.01) | |
| A61B 1/00 | (2006.01) | |
| A61B 1/313 | (2006.01) | |
| A61B 5/06 | (2006.01) | |
| A61B 34/20 | (2016.01) | |
| A61B 90/00 | (2016.01) | |
| A61B 34/00 | (2016.01) | |

(52) U.S. Cl.
CPC .......... *A61B 34/10* (2016.02); *A61B 1/00009* (2013.01); *A61B 1/3132* (2013.01); *A61B 5/06* (2013.01); *A61B 17/34* (2013.01); *A61B 17/3403* (2013.01); *A61B 17/3423* (2013.01); *A61B 34/20* (2016.02); *A61B 34/25* (2016.02); *A61B 90/39* (2016.02); *A61B 2017/3413* (2013.01); *A61B 2034/105* (2016.02); *A61B 2034/107* (2016.02); *A61B 2034/2051* (2016.02); *A61B 2034/2072* (2016.02); *A61B 2090/364* (2016.02); *A61B 2090/365* (2016.02); *A61B 2090/373* (2016.02)

(58) Field of Classification Search
None
See application file for complete search history.

(56) References Cited

U.S. PATENT DOCUMENTS

| | | | |
|---|---|---|---|
| 5,830,144 A * | 11/1998 | Vesely | A61B 34/20 600/459 |
| 5,833,611 A | 11/1998 | Tepper et al. | |
| 6,004,320 A | 12/1999 | Casscells et al. | |

(Continued)

FOREIGN PATENT DOCUMENTS

| | | |
|---|---|---|
| EP | 0965058 A1 | 12/1999 |
| JP | 2002204773 A | 7/2002 |

(Continued)

OTHER PUBLICATIONS

Extended European Search Report issued in Application No. 19151103. 9, dated May 15, 2019.

*Primary Examiner* — Katherine L Fernandez
(74) *Attorney, Agent, or Firm* — Carter, DeLuca & Farrell LLP

(57) ABSTRACT

A method for performing a surgical procedure includes generating, by a computing device, an anatomical map of a patient from a plurality of images; positioning a trocar obturator adjacent to the patient; calculating, by the computing device, a projected path of the trocar obturator; overlaying, by the computing device, the projected path of the trocar obturator with the anatomical map of the patient; and displaying the projected path of the trocar obturator and the anatomical map of the patient on a display device to define an augmented image.

20 Claims, 5 Drawing Sheets

(56) References Cited

U.S. PATENT DOCUMENTS

| | | |
|---|---|---|
| 6,120,496 A | 9/2000 | Whayne et al. |
| 6,203,493 B1* | 3/2001 | Ben-Haim ......... A61B 1/00135 |
| | | 600/117 |
| 7,029,435 B2 | 4/2006 | Nakao |
| 7,691,103 B2 | 4/2010 | Fernandez et al. |
| 8,317,814 B2 | 11/2012 | Karasawa et al. |
| 9,918,617 B2 | 3/2018 | Viola et al. |
| 2002/0045884 A1 | 4/2002 | Turovskiy et al. |
| 2005/0165272 A1 | 7/2005 | Okada et al. |
| 2006/0235457 A1 | 10/2006 | Belson |
| 2007/0249911 A1* | 10/2007 | Simon .................... G16H 70/20 |
| | | 600/300 |
| 2008/0119727 A1* | 5/2008 | Barbagli ............. A61B 8/0833 |
| | | 600/424 |
| 2013/0150710 A1* | 6/2013 | Zentgraf ................ A61B 5/062 |
| | | 600/424 |
| 2013/0197357 A1 | 8/2013 | Green et al. |
| 2015/0351860 A1* | 12/2015 | Piron .................... A61B 5/055 |
| | | 600/417 |
| 2016/0051127 A1* | 2/2016 | Yoshimura ............. A61B 34/30 |
| | | 600/109 |
| 2016/0073854 A1* | 3/2016 | Zeien ................... A61B 1/0676 |
| | | 600/109 |
| 2016/0120521 A1* | 5/2016 | Weingarten ............ A61B 6/487 |
| | | 600/424 |
| 2016/0287241 A1* | 10/2016 | Azevedo ............ A61B 17/0293 |
| 2017/0049517 A1* | 2/2017 | Felder .................... A61B 34/30 |
| 2017/0301088 A1* | 10/2017 | Bharat .................. A61B 34/20 |
| 2018/0338673 A1* | 11/2018 | Krimsky ................ A61B 34/20 |

FOREIGN PATENT DOCUMENTS

| | | |
|---|---|---|
| JP | 2003135388 A | 5/2003 |
| WO | 2005053517 A1 | 6/2005 |
| WO | 2007061386 A1 | 5/2007 |
| WO | 2010034107 A1 | 4/2010 |
| WO | 2017151904 A1 | 9/2017 |

* cited by examiner

SYSTEMS AND METHODS FOR LAPAROSCOPIC PLANNING AND NAVIGATION

BACKGROUND

Technical Field

The present disclosure relates to surgical systems and methods and, more particularly, to systems and methods for laparoscopic planning and navigation.

Background

In a laparoscopic surgical procedure, a small entrance incision is made in the skin through which a surgeon may introduce a hollow tube or access port (e.g., trocar). The access port allows the surgeon to insert a number of different surgical instruments therethrough for performing surgical procedures far removed from the incision. Proper placement of the access port is important in laparoscopic procedures and allows the surgeon to access the surgical site efficiently. In planning access port placement during a laparoscopic procedure, the surgeon often relies on rough measurements (e.g., anatomical landmarks, spatial reasoning, experience, etc.) to place the access port. If the access port is placed incorrectly, the surgeon may not be able to access the surgical site efficiently and may be prevented from fully visualizing the surgical field, which may require the surgeon to spend a significant amount of time repositioning instruments and tissue.

Therefore, a need exists for devices, systems, and methods for assisting a clinician with access port placement in laparoscopic surgical procedures.

SUMMARY

In accordance with an embodiment of the present disclosure, there is provided a method for performing a surgical procedure. The method includes generating, by a computing device, an anatomical map of a patient from a plurality of images; positioning a trocar obturator adjacent to the patient; calculating, by the computing device, a projected path of the trocar obturator; overlaying, by the computing device, the projected path of the trocar obturator with the anatomical map of the patient; and displaying the projected path of the trocar obturator and the anatomical map of the patient on a display device to define an augmented image.

In an embodiment, the method may further include determining the location of an incision site based on the augmented image.

In another embodiment, the method may further include positioning a rigid pad including a sensor array under the patient to establish a coordinate frame of reference of the patient.

In yet another embodiment, the method may further include affixing a position sensor to the trocar obturator to determine the position of the trocar obturator relative to the patient coordinate frame of reference.

In still yet another embodiment, the method may further include inserting an endoscope into the patient; and using at least one of a direction of view, a field of view, and a magnification of the endoscope to further refine, with the computing device, the augmented image.

In still yet another embodiment, the method may further include affixing a sleeve including a second position sensor about a shaft of the endoscope to determine the position of the endoscope relative to the patient coordinate frame of reference.

In an embodiment, generating the anatomical map of the patient may include performing pre-procedure imaging of the patient using one or more imaging modalities to create a pre-procedure anatomical map of the patient.

In another embodiment, generating the anatomical map of the patient may include performing real-time imaging of the patient during a surgical procedure.

In yet another embodiment, the method may further include processing, by the computing device, the real-time imaging of the patient and the pre-procedure imaging of the patient; overlaying, by the computing device, the pre-procedure imaging of the patient onto the real-time imaging of the patient to further refine the augmented image; and displaying, on the display device, the refined augmented image.

In accordance with another aspect of the present disclosure, there is provided a laparoscopic planning and navigation system. The system includes a real-time imaging system configured to capture image and video of a surgical site to define a surgical field of view, a sensor array positionable adjacent to a patient and configured to establish a patient coordinate frame of reference for the surgical site, a trocar obturator configured for insertion into a body cavity, an endoscope defining a field of view, a first position sensor attachable to the trocar obturator and a second position sensor attachable to the endoscope, a computing device including a processor and a memory, and a display device configured to display the projected path of each of the trocar obturator and the endoscope to define an augmented image on the display device.

In particular, the first and second position sensors are in communication with the sensor array and are configured to measure the respective positions of the trocar obturator and the endoscope relative to the patient coordinate frame of reference. In addition, the computing device is in communication with the sensor array and the first and second position sensors to determine the respective locations of the trocar obturator and the endoscope relative to the patient coordinate frame of reference. The computing device is configured to calculate a projected path of each of the trocar obturator and the endoscope relative to the patient coordinate frame of reference.

In an embodiment, the system further may include an elastomeric sleeve defining an inner surface. The inner surface of the elastomeric sleeve may be configured to receive the trocar obturator. The elastomeric sleeve may have the first position sensor affixed thereto.

In another embodiment, the system may further include a second elastomeric sleeve defining an inner surface. The inner surface of the second elastomeric sleeve may be configured to receive the endoscope. The second elastomeric sleeve may have the second position sensor affixed thereto.

In yet another embodiment, the first position sensor may be integrally formed with the trocar obturator.

In yet another embodiment, the second position sensor may be integrally formed with the endoscope.

In still yet another embodiment, the computing device may be configured to determine a location for a first incision site on the patient based on the projected path of the trocar obturator. In addition, the computing device may be configured to determine a location for a second incision site on the patient based on the projected path of the endoscope.

In an embodiment, the system may include a rigid pad positionable underneath the patient, the rigid pad including the sensor array.

In another embodiment, the computing device may be configured to overlay the projected path of each of the trocar obturator and the endoscope onto the surgical field of view defined by the real-time imaging system to further refine the augmented image.

In yet another embodiment, the computing device may be configured to correlate the field of view of the endoscope with the surgical field of view defined by the real-time imaging system to further refine the augmented image.

BRIEF DESCRIPTION OF THE DRAWINGS

Objects and features of the present disclosure will become apparent to those of ordinary skill in the art when descriptions thereof are read with reference to the accompanying drawings, of which.

DETAILED DESCRIPTION

Figure 1:
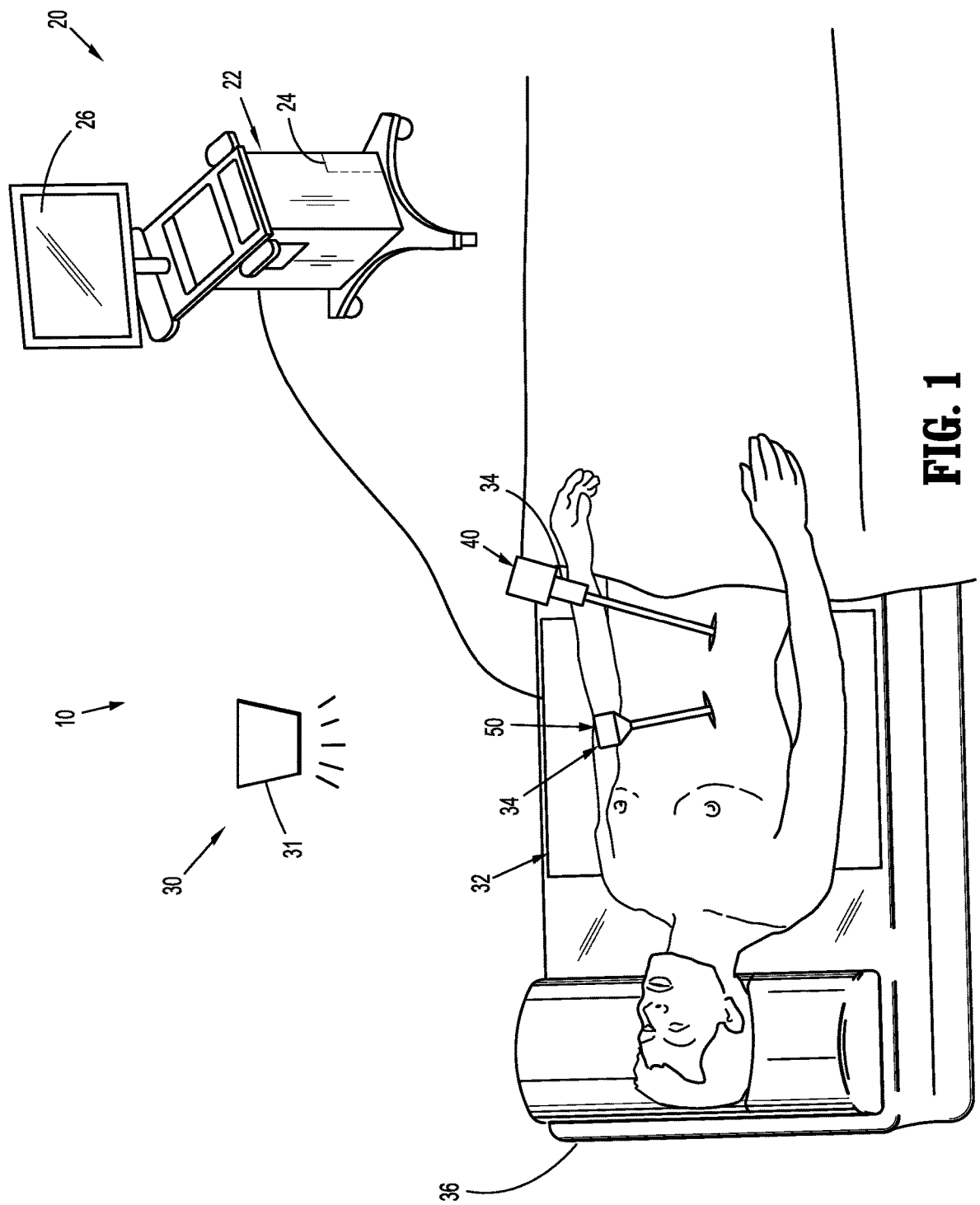
FIG. 1 is a schematic diagram of a laparoscopic planning and navigation system in accordance with an embodiment of the present disclosure.

Embodiments of the present disclosure are described in detail with reference to the drawings in which like reference numerals designate identical or corresponding elements in each of the several views. As used herein, the term "clinician" refers to a doctor, nurse, or other care provider and may include support personnel. In the following description, well-known functions or constructions are not described in detail to avoid obscuring the present disclosure in unnecessary detail.

The laparoscopic navigation and planning system of the present disclosure enables a clinician to accurately determine access port (e.g., trocar obturator) placement locations on a patient in a laparoscopic procedure. For example, a trocar obturator may include a position sensor such that the trocar obturator's position can be identified within a surgical field. An augmented image of the surgical field may be viewable on a display, depicting the projected path (e.g., the trajectory) of the trocar obturator, and tissue structures within the projected path of the trocar obturator. Thus, the clinician can accurately determine an incision site on a patient for the trocar obturator, thereby reducing surgical errors, the need for additional incisions, operating time, etc.

Referring initially to FIG. 1, an illustration of a laparoscopic navigation and planning system 10 in accordance with the present disclosure is shown and generally includes an a workstation 20, a tracking system 30, an endoscope 40, and a trocar obturator 50.

Workstation 20 includes a computing device 22, a memory 24, and a display 26. The computing device 22, in turn, includes a processor and memory, such as random access memory (RAM). The processor may be any suitable processor adapted to perform or execute techniques, operations, applications, algorithms, programs, and/or instructions described herein. The processor may include one or more central processing units (CPUs), application specific integrated circuits (ASICs), field programmable gate arrays (FPGAs), digital signal processors (DSPs), microprocessors, or any combination thereof.

Memory 24 may be any type of hardware device used to store data. Memory 24 may include volatile memory, such as random access memory (RAM) (e.g., dynamic random access memory (DRAM), static random access memory (SRAM), etc.). Memory 24 may include non-volatile memory, such as read-only memory (ROM), erasable programmable read-only memory (EPROM), electrically erasable programmable read-only memory (EEPROM), non-volatile RAM (NVRAM), etc. Memory 24 may also include magnetic, optical, or electrical media.

Display 26 is communicatively connected to computing device 22 of workstation 20. Display 26 may be any device configured to display at least one output of computing device 22 (e.g., a touch screen display, a light-emitting diode (LED) display, a liquid-crystal display (LCD), an organic light-emitting diode (OLED) display, a plasma display panel (PDP), etc.). Computing device 22, which may include one or more graphics or video processors, may be configured to cause display 26 to display images and video of a surgical environment (e.g., real time, augmented, virtual, etc.), anatomical patient imaging, locations or possible locations of surgical instruments and tools within a surgical environment, patient data, etc., as will be described below.

Tracking system 30 includes a real-time imaging device 31, a sensor array 32, and one or more position sensors 34. Real-time imaging device 31, sensor array 32, and position sensors 34 are communicatively connected to computing device 22 of workstation 20 to generate one or more images and/or video of a surgical field, to be displayed on display 26 of workstation 20. In embodiments, tracking system 30 may be any type of imaging/tracking system known in the art, such as an optical navigation system, electromagnetic tracking system, an ultrasonic tracking system, or any combination thereof.

Real-time imaging device 31 may be any type of real-time imaging system such as, magnetic resonance imaging (MRI), ultrasound, computed tomography (CT), positron emission tomography (PET), etc., for capturing images and/or video of a surgical field. Real-time imaging device 31 may also include one or more cameras that define a field of view.

Position sensors 34 are connected to, secured to, and/or integrated with endoscope 40 and trocar obturator 50 to determine the position of endoscope 40 and trocar obturator 50 relative to the patient coordinate frame of reference, as will be described below. In embodiments, position sensor 34 may be any suitable type of position sensor, including electromagnetic, optical, acoustic, electrical field, radio frequency (RF), an accelerometer, etc.

Sensor array 32 of tracking system 30 is positioned near (e.g., underneath, next to, etc.) a patient to establish a patient coordinate frame of reference. In embodiments, sensor array 32 may be included in a pad, e.g., a rigid pad, positioned between the patient and operating table 36.

Figure 2:
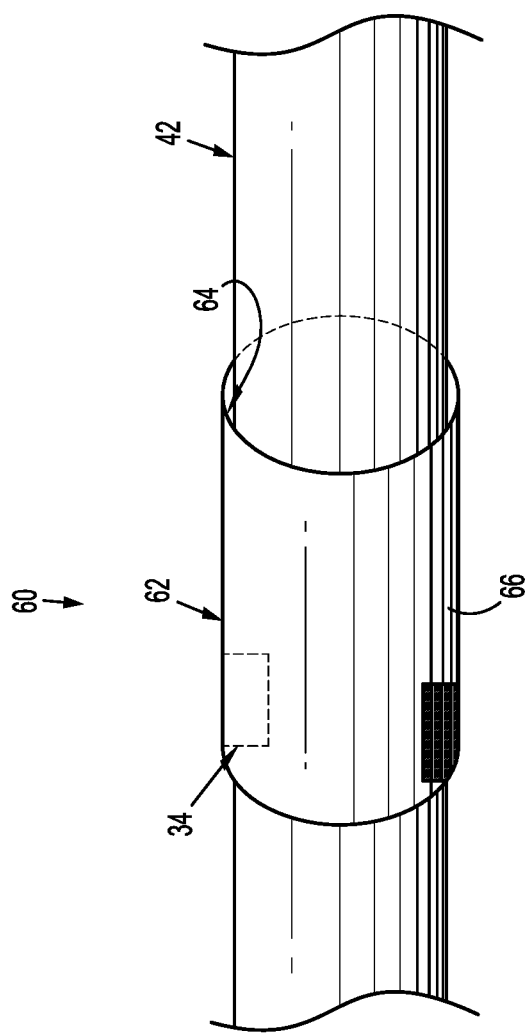
FIG. 2 is a position-sensing sleeve of the laparoscopic planning and navigation system of FIG. 1.

With reference to FIG. 2, position sensor 34 is included in a sheath or sleeve 60. Sleeve 60 includes a body 62 defining an inner surface 64 and an outer surface 66. Sleeve 60 is positionable about a portion of any surgical instrument or tool (e.g., endoscope 40, trocar obturator 50, etc.). Sleeve 60 may be formed from a flexible and/or conformable material, such as an elastomer. Alternatively, sleeve 60 may be formed from a thermoplastic, polymer, or any rigid or semi-rigid material.

Although sleeve 60 is shown as having a substantially cylindrical shape, any suitable shape is contemplated, such as rectangular, triangular, or the like. In embodiments, position sensor 34 of sleeve 60 may be recognizable by sensor array 32 to establish the position of sleeve 60 relative to the patient coordinate frame of reference. Position sensor 34 of sleeve 60 may be hard wired to computing device 22, or alternatively, may be in wireless communication with computing device 22.

Endoscope 40 is operatively connected to workstation 20 and is configured for insertion into a body cavity for viewing a surgical site. Endoscope 40 defines a field of view from within the body cavity of the patient of the surgical site, which is viewable as images and/or video on display 26 of workstation 20. Sleeve 60 is positionable about a shaft 42 of endoscope 40 (FIGS. 1 and 2). Position sensor 34 of sleeve 60 of endoscope 40 communicates with sensor array 32 such that the position and orientation of endoscope 40 can be established relative to the patient coordinate frame of reference. In embodiments, endoscope 40 may be any type of tubular instrument used to view the body of a patient such as a laparoscope, nephroscope, bronchoscope, arthroscope, colonoscope, etc.

Trocar obturator 50 includes an integrated position sensor 34 that communicates with sensor array 32 such that the position and orientation of trocar obturator 50 can be established relative to the patient coordinate frame of reference. Additionally or alternatively, sleeve 60 including position sensor 34 may be attached or secured to trocar obturator 50 to establish the position and orientation of trocar obturator 50 relative to the patient coordinate frame of reference. Trocar obturator 50 may be any suitable medical device (e.g., a trocar, tube, cannula, seal, stylus, introducer, obturator, etc.) configured to provide access to a body cavity during a laparoscopic procedure.

Figure 3:
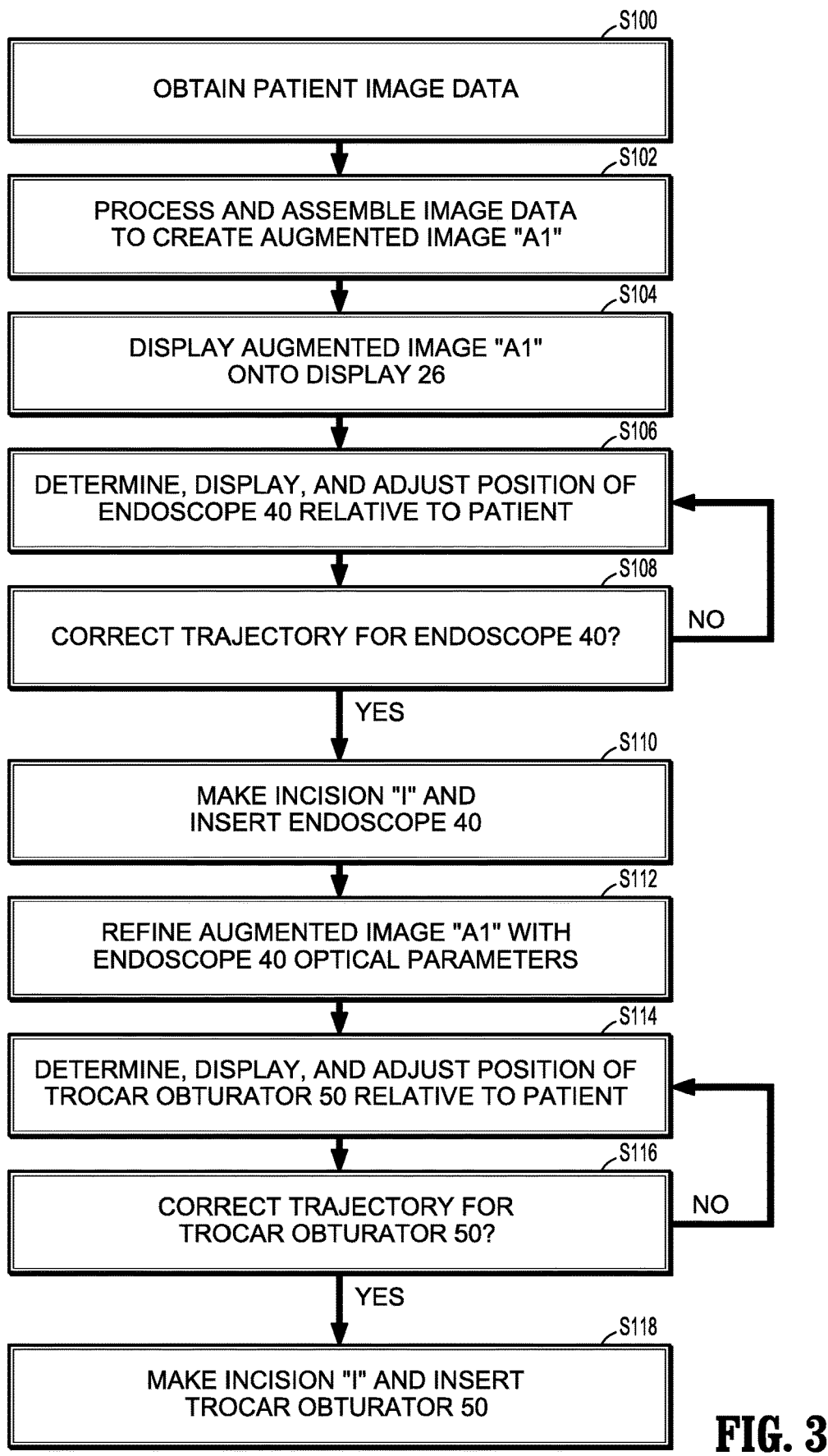
FIG. 3 is a flowchart illustrating a method of performing a surgical procedure in accordance with the present disclosure.

Referring now to FIG. 3, a method in accordance with the present disclosure is described. The method of FIG. 3, although necessarily illustrated and described in an order, is not intended to have any limiting effect or to imply any particular order. To this end, the methods illustrated and described herein may include some or all of the features described and may be implemented in any suitable order. In addition, although laparoscopic procedures are referenced herein, it should be appreciated that the method of FIG. 3 is applicable for any type of procedure (e.g., open surgical procedures).

In use, in step S100, as part of the planning phase, a series of pre-procedure images of the patient (e.g., of the abdominal cavity, surgical site, etc.) are obtained using one or more imaging modalities (e.g., MRI, CT, ultrasound, PET, etc.) to create a pre-procedure anatomical map of the patient. The imaging data is then loaded onto workstation 20, which computing device 22 utilizes for generating and viewing a three-dimensional (3D) anatomical map or model of the patient on display 26 of workstation 20. The 3D anatomical map enables the identification of the target tissue structures "T" (FIGS. 4 and 5), e.g., automatically, semi-automatically or manually. More specifically, computing device 22 processes and assembles the pre-procedure imaging data into a 3D volume, which is then utilized to generate the 3D anatomical map of the patient and stored in memory 24.

Figure 4:
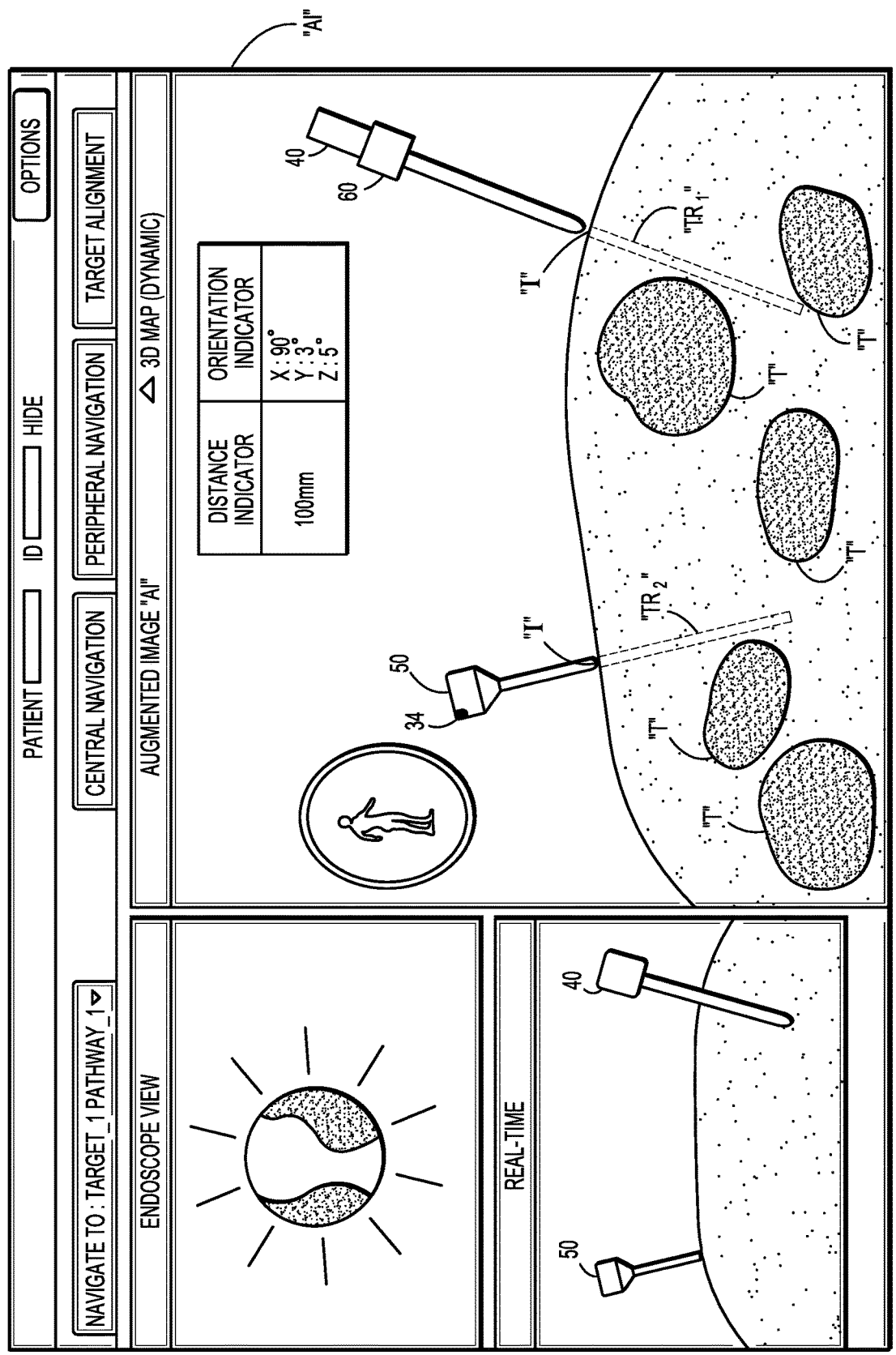
FIG. 4 is an augmented image of a surgical field depicting a projected path of a trocar obturator and an endoscope of the laparoscopic planning and navigation system of FIG. 1.
Figure 5:
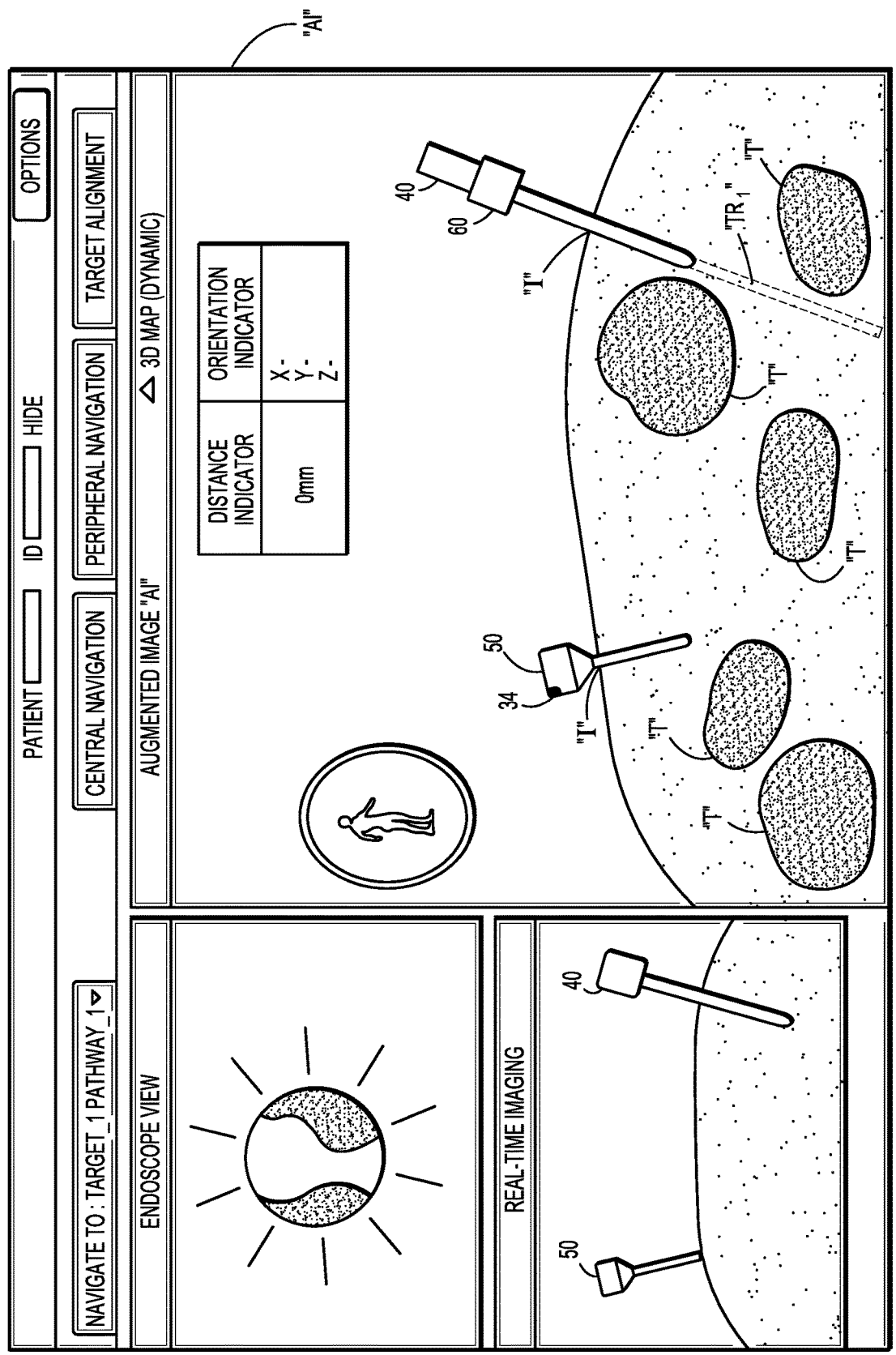
FIG. 5 is an augmented image of the surgical field with the endoscope and the trocar obturator of the laparoscopic planning and navigation system of FIG. 1 inserted into a patient.

During the procedure phase, in step S100, real-time imaging device 31 (FIG. 1) of tracking system 30 captures real-time images and video of the surgical field, and sensor array 32 is placed adjacent or under the patient to establish a coordinate frame of reference of the patient. In step S102, computing device 22 processes and overlays the real-time image data from real-time imaging device 31 with the pre-procedure 3D model image data stored in memory 24. Specifically, the pre-procedure 3D anatomical map is overlaid onto the real-time image data from real-time imaging device 31 and combined into a 3D volume, with the resulting "augmented reality" or augmented image "AI" (FIG. 4) of the patient's anatomical map displayed (e.g., as images and video) in real-time on display 26 of workstation 20. Computing device 22, using one or more programs, identifies tissue structures "T" (e.g., luminal networks, organs, muscle, etc.) and marks their location such that the clinician can readily identify the tissue structures "T" (e.g., and other sites of interest) in real time. As shown in FIG. 4, the tissue structures "T" are overlaid onto the patient and viewable in the augmented image "AI." In step S104, the resulting augmented image "AI" is displayed on display 26 of workstation 20, such that the clinician can view the anatomical map of the patient and surgical instruments and tools relative to the patient, in real-time on display 26 during the procedure.

In step S106, endoscope 40 is then positioned near the patient. Position sensor 34 of endoscope 40 coordinates with sensor array 32 such that the position and orientation of endoscope 40 is established relative to the patient coordinate frame of reference. The position and orientation of endoscope 40 is viewable on display 26 of workstation 22, such that the clinician can view, in real-time, the location of endoscope 40 relative to the patient. In addition, position sensor 34 communicates with computing device 22 of workstation 20 such that the projected path or trajectory "TR$_1$" (FIG. 4) of endoscope 40 is added to augmented image "AI" and viewable on display 26 of workstation 20. In step S108, if the trajectory "TR$_1$" of endoscope 40 is correct, then, in step S110, the clinician can make an incision "I" in the patient to place the endoscope 40 therein and continue the procedure. In step S108, if the trajectory "TR$_1$" of endoscope 40 is incorrect, the clinician, in step S106, can make further adjustments, using display 26 of workstation 20 to adjust the trajectory "TR$_1$" of endoscope 40. Therefore, the clinician can determine the appropriate location for an incision through which endoscope 40 may be inserted, while avoiding critical tissue structures "T," reducing surgical errors, the need for additional incisions, operating time, etc.

Once the endoscope 40 is inserted into the patient, endoscope 40 captures images and video of a surgical site. In step S112, computing device 22 of workstation 20 processes the optical parameters (e.g., direction of view, field of view, magnification, etc.) of endoscope 40, and then assembles the optical parameters of endoscope 40 into the patient imaging data to further refine, in real-time, the augmented image "AI," e.g., to increase the accuracy of the augmented image "AI." Specifically, the pre-procedure 3D-model imaging data of the patient, the imaging data received from tracking system 30 during the procedure, and the optical parameters of the endoscope 40 are assembled into a cohesive, augmented image "AI," which is viewable on display 26 of workstation 20.

In step S114, using the augmented image "AI," the clinician determines the appropriate location for placing trocar obturator 50. The position sensor 34 of trocar obturator 50 and sensor array 32 of tracking system 30 permits the clinician to view, using display 26 of workstation 20, the position and orientation of trocar obturator 50 such that the clinician can view, in real-time, the location of trocar obturator 50 relative to the patient coordinate frame of reference. Position sensor 34 communicates with computing device 22 of workstation 20 such that the intended trajectory "TR$_2$" of trocar obturator 50 is added to augmented image "AI" and viewable on display 26 of workstation 20. In step S116, if the trajectory "TR$_2$" of trocar obturator 50 is correct, then, in step S118, the clinician can make an incision "I" in the patient to place the trocar obturator 50 therein and continue the procedure. In step S116, if the trajectory "TR$_2$" of trocar obturator 50 is incorrect, then in step S114, the clinician can make further adjustments, using display 26 of workstation 20 to adjust the trajectory "TR$_2$" of trocar obturator 50. Therefore, the clinician can determine the appropriate location for an incision through which trocar obturator 50 may be inserted, while avoiding critical tissue structures "T," reducing surgical errors, the need for additional incisions, operating time, etc.

The access devices and/or surgical systems described herein can be utilized with powered surgical instruments, robotic surgical instruments, and/or be incorporated in a robotic surgical system.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A method for performing a surgical procedure comprising:
   generating, by a computing device, an anatomical map of a patient from a plurality of images;
   positioning a trocar obturator adjacent to the patient;
   calculating, by the computing device, a projected path of the trocar obturator;
   overlaying, by the computing device, the projected path of the trocar obturator with the anatomical map of the patient;
   displaying the projected path of the trocar obturator and the anatomical map of the patient on a display device to define an augmented image;
   establishing a coordinate frame of reference of the patient;
   affixing a position sensor to the trocar obturator to determine a position of the trocar obturator relative to the patient coordinate frame of reference;
   positioning an endoscope adjacent the patient;
   calculating, by the computing device, a trajectory of the endoscope;
   displaying the trajectory of the endoscope on the augmented image, wherein a position and an orientation of the endoscope relative to the patient coordinate frame of reference is displayed on the augmented image;
   adjusting the displayed trajectory of the endoscope on the augmented image prior to making an incision in the patient if the trajectory of the endoscope is incorrect;
   making the incision in the patient based on the displayed trajectory of the endoscope on the augmented image; and
   inserting the endoscope into the patient through the incision,
   wherein a sleeve formed of a flexible material is selectively affixed about a shaft of the endoscope such that a portion of the shaft extends distally through the sleeve, the sleeve including a second position sensor to determine the position and the orientation of the endoscope relative to the patient coordinate frame of reference.

2. The method of according to claim 1, further including positioning a rigid pad including a sensor array under the patient to establish the patient coordinate frame of reference.

3. The method according to claim 1, further comprising:
   using at least one of a direction of view, a field of view, and a magnification of the endoscope to refine, with the computing device, the augmented image.

4. The method according to claim 1, wherein generating the anatomical map of the patient includes performing pre-procedure imaging of the patient using one or more imaging modalities to create a pre-procedure anatomical map of the patient.

5. The method according to claim 4, wherein generating the anatomical map of the patient includes performing real-time imaging of the patient during the surgical procedure.

6. The method according to claim 5, further comprising:
   processing, by the computing device, the real-time imaging of the patient and the pre-procedure imaging of the patient;
   overlaying, by the computing device, the pre-procedure imaging of the patient onto the real-time imaging of the patient to refine the augmented image; and
   displaying, on the display device, the refined augmented image.

7. The method according to claim 1, wherein affixing the position sensor to the trocar obturator includes determining an orientation of the trocar obturator relative to the patient coordinate frame of reference.

8. The method according to claim 1, further comprising adjusting the trajectory of the endoscope.

9. A method for performing a surgical procedure comprising:
   generating, by a computing device, an anatomical map of a patient;
   positioning a trocar obturator adjacent to the patient;
   calculating, by the computing device, a projected path of the trocar obturator;
   overlaying, by the computing device, the projected path of the trocar obturator with the anatomical map of the patient;
   displaying the projected path of the trocar obturator and the anatomical map of the patient on a display device to define an augmented image;
   establishing a coordinate frame of reference of the patient;
   affixing a position sensor to the trocar obturator to determine a position of the trocar obturator relative to the patient coordinate frame of reference;
   positioning a surgical instrument adjacent the patient;

calculating, by the computing device, a trajectory of the surgical instrument;

displaying the trajectory of the surgical instrument on the augmented image, wherein a position and an orientation of the surgical instrument relative to the patient coordinate frame of reference is displayed on the augmented image;

adjusting the displayed trajectory of the surgical instrument on the augmented image prior to making an incision in the patient if the trajectory of the surgical instrument is incorrect;

making the incision in the patient based upon the displayed trajectory of the surgical instrument on the augmented image; and inserting the surgical instrument into the patient through the incision, wherein a second position sensor is disposed on the surgical instrument and is configured to determine the position and the orientation of the surgical instrument relative to the patient coordinate frame of reference.

10. The method of claim 9, wherein defining the augmented image includes generating a 3D volume of the patient.

11. The method of claim 9, further including:
using at least one of a direction of view, a field of view, and a magnification of the surgical instrument to refine, with the computing device, the augmented image.

12. The method of claim 9, further including overlaying identified tissue structures onto the augmented image to refine, with the computing device, the augmented image.

13. The method of claim 9, further including displaying, on the display device, at least one of a location of the surgical instrument and patient data.

14. The method of claim 9, wherein the augmented image is displayed on the display device and refined, with the computing device, in real time.

15. The method of claim 9, further including positioning a rigid pad including a sensor array under the patient to establish the patient coordinate frame of reference.

16. The method according to claim 9, wherein generating the anatomical map of the patient includes performing pre-procedure imaging of the patient using one or more imaging modalities to create a pre-procedure anatomical map of the patient.

17. The method according to claim 16, wherein generating the anatomical map of the patient includes performing real-time imaging of the patient during the surgical procedure.

18. The method according to claim 17, further including:
processing, by the computing device, the real-time imaging of the patient and the pre-procedure imaging of the patient;
overlaying, by the computing device, the pre-procedure imaging of the patient onto the real-time imaging of the patient to refine the augmented image; and
displaying, on the display device, the refined augmented image.

19. The method according to claim 9, wherein affixing the position sensor to the trocar obturator includes determining an orientation of the trocar obturator relative to the patient coordinate frame of reference.

20. The method according to claim 9, further including adjusting the trajectory of the surgical instrument.

* * * * *